United States Patent [19]

Ablaza

[11] Patent Number: 4,632,113
[45] Date of Patent: Dec. 30, 1986

[54] SUTURE FOR CARDIOVASCULAR SURGERY

[76] Inventor: Sariel G. G. Ablaza, 3600 Conshohocken Ave., Philadelphia, Pa. 19131

[21] Appl. No.: 778,894

[22] Filed: Sep. 23, 1985

[51] Int. Cl.$^4$ .............................................. A61L 17/00
[52] U.S. Cl. ................................................... 128/335.5
[58] Field of Search ..................... 128/334 R, 335.5; 623/2

[56]  References Cited

U.S. PATENT DOCUMENTS 2,591,063  5/1949  Goldberg .......................... 128/335.5
4,069,825  1/1978  Akiyama ........................... 128/335.5

FOREIGN PATENT DOCUMENTS 1031649  5/1978  Canada ............................. 128/335.5

OTHER PUBLICATIONS

The Journal of Thoracic & Cadiovascular Surgery, vol. 73, No. 4, Apr. 1977, pp. 589–595.

Primary Examiner—Richard C. Pinkham
Assistant Examiner—Gary Jackson
Attorney, Agent, or Firm—Arthur A. Jacobs

[57]  ABSTRACT

A surgical suture device comprising a backer in the form of a streamlined bead fixedly connected to opposing ligature strands, the free ends of the ligature strands being connected to surgical needles; the streamlining of the backer eliminating excess surfaces and corners which tend to promote the formation of blood clots, and the fixed relationship between the backer and the ligature strands preventing twisting of the backer and tangling of the ligature strands.

3 Claims, 6 Drawing Figures

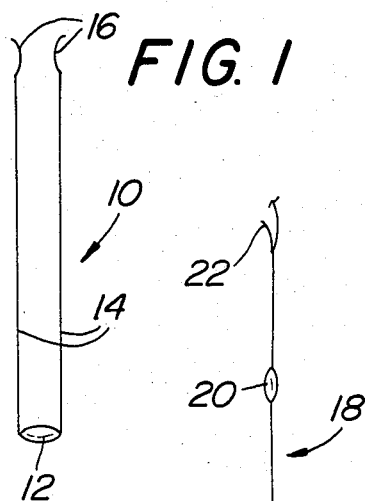
FIG. 1
FIG. 2
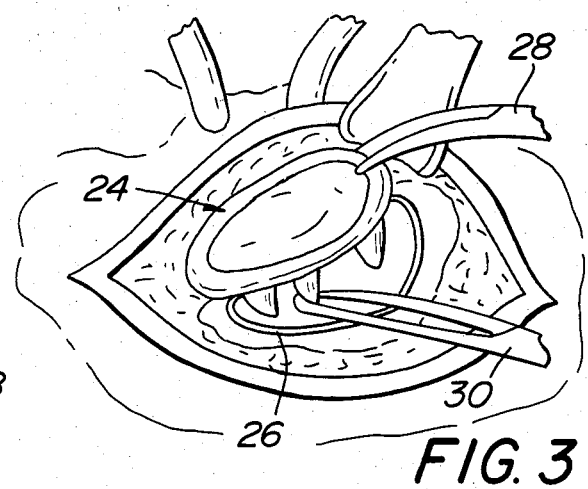
FIG. 3
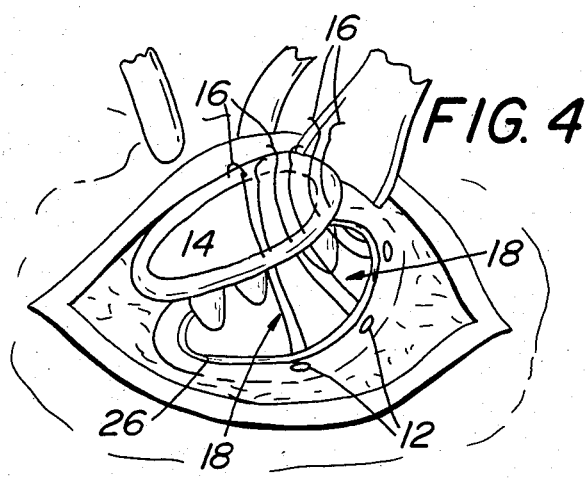
FIG. 4
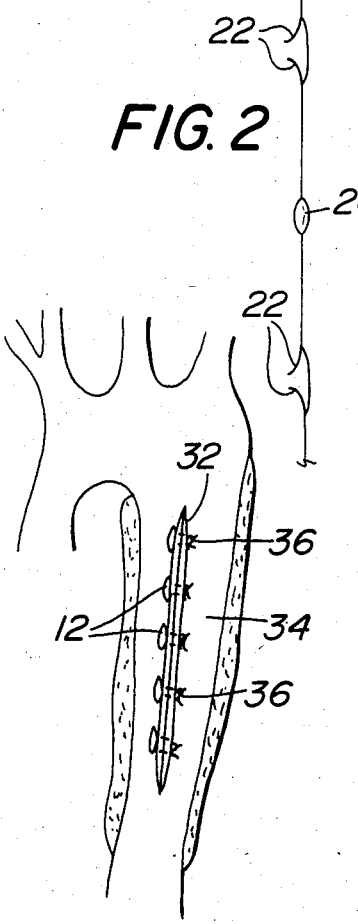
FIG. 6
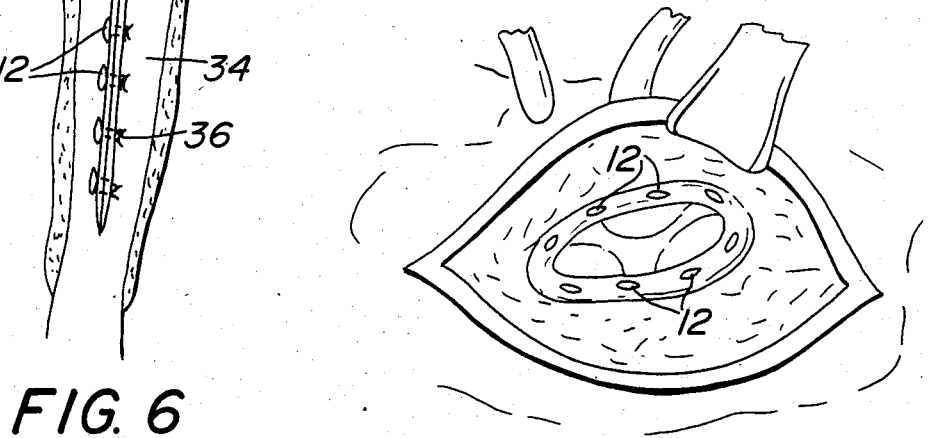
FIG. 5

SUTURE FOR CARDIOVASCULAR SURGERY

This invention relates to surgical sutures, and it particularly relates to unitary suture assemblies utilizable in cardiovascular surgery.

Among the commonly used types of sutures in cardiovascular surgery are the so-called backed mattress sutures which comprise a rectangular backer or "mattress" made of a felt-like material, usually Dacron or Teflon, through which is slidably looped a ligature in such manner that the bridge portion of the loop is on one flat side of the backer while the two arms or strands thereof pass through individual spaced holes on the opposite flat face of the backer. A needle is attached to the free ends of each of the two arms or strands of the ligature.

In use, the needles are passed through the two areas to be sutured, such as a valve ring and the adjacent tissue, carrying their respective ligature strands with them in such manner that the backer abuts the underside of one of the areas. The strands are then pulled tight and knotted in place against the opposite surface of the other area.

The above-described suture procedure results in an effective connection, with the backer acting as a reinforcement for the tissue or other parts being joined. However, it is subject to various disadvantages. For example, the felt-like texture of the backer may cause it to be inundated with more blood than it is able to absorb. The excess blood may clot on the corners and straight sides and edges of the backer, and these clots may then break off with obviously serious damage to the cardiovascular system.

Another significant disadvantage of these prior type mattress sutures was that the backer was slidable on the ligature and, since the ligature was looped through the backer loosely, there was a tendency for the loop to twist or tangle adjacent the backer. This often caused the backer to twist onto its side or even up-end itself. This seriously interferred with its functioning.

Another disadvantage of the prior type mattress sutures was the fact that each assembly had to be separately made and separately used. It required time and effort to sort out and use these individual assemblies, a significant factor, since even the smallest additional time and effort is often critical during an operation.

It is an object of the present invention to overcome the above and other disadvantages by providing a suture assembly that includes a backer that is not prone to excess absorption of blood and does not tend to cause blood clot formation.

Another object of the present invention is to provide a suture assembly comprising a backer and a ligature in which there is no tendency of the ligature to tangle and no tendency of the backer to twist or become up-ended.

Yet another object of the present invention is to provide a unitary progression of suture assemblies whereby a suture assembly is readily and quickly available whenever required.

Other objects and many of the attendant advantages of this invention will be readily appreciated as the same becomes better understood by reference to the following description when read in conjunction with the accompanying drawings wherein:

FIG. 1 is an elevational view of a single suture assembly.

FIG. 2 is an elevational view of a strand of suture assemblies.

FIG. 3 is a perspective view showing the preliminary stage of a mitral valve replacement prior to suturing.

FIG. 4 is a perspective view of the suturing stage utilizing suture assemblies embodying the present invention.

FIG. 5 is a perspective view showing the valve replaced.

FIG. 6 is a perspective view showing the suture assembly of this invention utilized to close a slit in the aorta.

Referring now in greater detail to the drawings wherein similar reference characters refer to similar parts, there is shown in FIG. 1 a suture assembly generally designated 10, comprising a bead 12, made of Dacron or the like, and having a generally streamlined contour free from abrupt edges or walls. Extending from opposite ends of the bead 12 are ligature strands 14, made of nylon, Dacron, or the like, each of which is provided at its free end with a needle 16. The bead 12 is immovably fixed to the strands 14 in any manner desired, as by integral molding, knotting in place, or otherwise.

The assembly 10 is preferably formed as an integral segment of a continuous ligature line, generally designated 18, as shown in FIG. 2. The line 18 comprises a continuous strand having beads 20, preferably, but not necessarily, of the same material, interspersed therealong at predetermined distances, as, for example, between about 24 to 30 inches apart. Intermediate each pair of beads are provided a pair of spaced-apart needles 22. When it is desired to utilize an individual assembly, the endmost assembly is removed from the line 18 by cutting between the needles of the next adjacent pair of needles, resulting in an assembly such as shown in FIG. 1.

By means of the continuous suture line, such as shown at 18, which can be rolled up, folded over, or otherwise packed as a unit, it is a simple matter to sever a suture assembly therefrom whenever needed, with no delay, fuss or bother—which can be highly important during complex heart surgery.

The streamlined beads (shown at 12 in FIG. 1 and 20 in FIG. 2) are not only sufficiently solid to prevent undue saturation by blood, but they do not provide the excess surfaces and abrupt corners and walls which promote a tendency for blood clotting.

The manner in which these suture assemblies may be used is illustrated in FIGS. 3 to 6. In FIGS. 3, 4 and 5, the suture assemblies are used in the replacement of a mitral valve with a porcine valve. FIG. 3 shows the porcine valve 24 being set in place within ring 26 by forceps 28 and 30. In FIG. 4, the suture assemblies 18 are used by passing the needles 16 through the ring and the rim of the valve 24 to draw the ligature strands 14 through with them. The backers 12 are then pulled flush against the ring 26 and the strands are pulled tight and knotted to form the suture. The valve is shown sutured in place in FIG. 5.

FIG. 6 illustrates the use of the suture assemblies in the closing of a slit in the aorta. The slit 32 in the aorta 34 is pulled together so that the lips thereof are in abutment. A series of sutures are then made with the backers 12 pulled tight against one of the lips and the strands of the corresponding ligatures being knotted against the other lip, as shown at 36.

The solid backers 12 not only are not prone to inundation by blood but their streamlined contours eliminates any excess surfaces and corners which tend to promote blood clotting. Furthermore, the fixed relationship between the ligature and the backer prevents any relative movement therebetween and, therefore, eliminates any tendency to tangling of the ligature and twisting, angling or overturning of the backer.

The invention of claimed is:

1. A surgical suture assembly comprising a ligature line, a series of backers arranged in spaced relationship to each other linearly of said line, said backers having streamlined contours and being fixed to said line, and a pair of surgical needles fixed to said line between each pair of adjacent backers, the needles of each pair being spaced from each other linearly of said line a sufficient distance to permit severance therebetween.

2. The suture assembly of claim 1 wherein said backers are relatively non-liquid absorbent.

3. The suture assembly of claim 1 wherein said backers are integral with said ligature line.

* * * * *